United States Patent
Navarro Medrano et al.

(10) Patent No.: US 9,000,047 B2
(45) Date of Patent: Apr. 7, 2015

(54) COMPOUND INHIBITING ACTIVATION OF THE ENZYME ERK 1/2 TO BE USED IN THE TREATMENT OF NEURODEGENERATIVE ILLNESSES

(75) Inventors: Pilar Navarro Medrano, Alcobendas (ES); Elisabet Gregori Puigjane, Alcobendas (ES); Marisol Montolio Del Olmo, Alcobendas (ES); Ana Jimenez Redondo, Alcobendas (ES); Jordi Mestres Lopez, Alcobendas (ES)

(73) Assignee: Farmalider, S.A., Madrid (ES)

( * ) Notice: Subject to any disclaimer, the term of this patent is extended or adjusted under 35 U.S.C. 154(b) by 143 days.

(21) Appl. No.: 13/699,355

(22) PCT Filed: May 24, 2010

(86) PCT No.: PCT/ES2010/000228
§ 371 (c)(1),
(2), (4) Date: Nov. 21, 2012

(87) PCT Pub. No.: WO2011/147999
PCT Pub. Date: Dec. 1, 2011

(65) Prior Publication Data
US 2013/0065966 A1    Mar. 14, 2013

(51) Int. Cl.
*A61K 31/13* (2006.01)
*A01N 33/02* (2006.01)
*A61K 31/137* (2006.01)

(52) U.S. Cl.
CPC .............. *A61K 31/13* (2013.01); *A61K 31/137* (2013.01)

(58) Field of Classification Search
CPC ............................. A61K 31/13; A61K 31/137
USPC .......................................... 514/659; 564/456
See application file for complete search history.

(56) References Cited

U.S. PATENT DOCUMENTS 4,061,774 A    12/1977  Chakrabarti et al.
2004/0087658 A1*  5/2004  Moebius ....................... 514/579

OTHER PUBLICATIONS

Gemignani et al., "Pharmacological study of two new adamantane derivatives", 1979, Farmaco—Edizione Scientifica, vol. 34, Issue: 12, pp. 1029-1038.*
Parsons et al., "Comparison of the potency, kinetics and voltage-dependency of a series of uncompetitive NMDA receptor antagonists in vitro with anticonvulsive and motor impairment activity in vivo", Oct. 1995, Neuropharmacology, vol. 34, Issue: 10, pp. 1239-1258.*
Bayat et al., "DFT-Based QSAR Prediction of 1-Octanol/Water Partition Coefficient of Adamantine derivatives drugs", J. Chem. Pharm. Res., 2010, vol. 2, Issue 6, pp. 416-423.*
Montolio et al., "Identification of Small Molecule Inhibitors of Amyloid β—Induced Neuronal Apoptosis Acting through the Imidazoline I2 Receptor", J. Med. Chem., Oct. 2012, vol. 55, pp. 9838-9846.*
Supplementary European Search Report for EP 10-85-2025, dated Sep. 30, 2013.
Adamantane and Protoadamantanealkanamines as Potential Anti-Parkinson Agents:, Journal of Medicinal Chemistry, American Chemical Society, vol. 19, No. 7, Jan. 1, 1976; p. 967-969.

* cited by examiner

*Primary Examiner* — My-Chau T Tran
(74) *Attorney, Agent, or Firm* — Cook Alex Ltd.

(57) ABSTRACT

The present invention relates to a compound of formula (I) for use as a medicine, in particular for use in the treatment of diseases mediated by the actvation of the protein kinase Erk1/2, such as neurogenerative illnesses like Alzheimer's and related dementia, epilepsy, Parkinson's disease, Huntington's disease, or stroke, and likewise relates to the pharmaceutical compositions containing said compound. The compound of formula (I) effectively inhibits the activation of the enzyme Erk1/2 induced by the tissue plasminogen activator (TPA) and also effectively inhibits the apoptosis generated by the β-amyloid peptide.

11 Claims, No Drawings

COMPOUND INHIBITING ACTIVATION OF THE ENZYME ERK 1/2 TO BE USED IN THE TREATMENT OF NEURODEGENERATIVE ILLNESSES

FIELD OF THE INVENTION

The present invention belongs to the field of medical chemistry and relates to the compound of formula (I), a primary triclyclic amine, which inhibits the tPA-induced activation of the enzyme Erk 1/2 and is promising for, the treatment of neurodegenerative illnesses, such as, for example, Alzheimer's disease (AD) and epilepsy, and also relates to pharmaceutical compositions that contain it.

PRIOR ART

Mitogen-activated protein kinases (MAPK) in mammals are serine/threonine kinases which mediate the intracellular signal transduction pathways. The members of the MAP kinase family share similar sequences and conserved structural domains, and include extracellular-signal-regulated kinases (Erk), Jun N-terminal kinases (JNK) and p38 kinases.

Erks are a widely-expressed type of protein kinases involved in various functions, which include the regulation of meiosis, mitosis and post-mitotic functions in differentiated cells.

The metabolism of Erks is activated by many different stimuli, including growth factors, mitogens, cytokines, viral infections and carcinogenic agents.

Neurodegenerative illnesses represent a broad chapter within neurological pathology. This heading includes a group of illnesses with an unknown cause whose common attribute is the progressive development of symptoms, which reflects the gradual disintegration of one or several parts of the nervous system. They all present some common clinical characteristics; namely, an insidious onset and a progressive development, without any remissions. The neurodegenerative illnesses that affect human beings include Alzheimer's disease, epilepsy, Parkinson's disease, Huntington's disease and strokes.

Neurodegenerative illnesses do not have an etiological treatment and therapeutic actions are symptomatic in some cases and palliative in all cases. They generate a disability and a terrible physical and psychic suffering amongst those who suffer from it and their families.

The socio-economic repercussions are very significant, since the process of the illness itself is aggravated by the psychic impact, the decline in the quality of life, the inability to work, the loss of social skills, the physical and psychic burden on these patients' caregivers and the enormous economic cost of the social and health care for all these people.

The article by M. G. Medina et al., EMBO J., 2005, 24, 1706-1716, shows that the toxicity of the β-amyloid peptide is mediated by the tissue plasminogen activator (tPA), through the activation of the extracellular-signal-regulated kinase enzyme (Erk 1/2), for which reason a blockage of the toxicity of tPA would be associated with a blockage of the toxicity of the β-amyloid peptide.

The review article by S. O. Bachurin, *Medicinal Chemistry Approaches for the Treatment and Prevention of Alzheimer's Disease, Med. Res. Reviews,* 2003, 23 (1), 48-88, states that new strategies in the search for new therapeutic approaches are based on the morphological and biochemical characteristics of AD, and include the identification of compounds that interfere with the metabolism of the β-amyloid peptide, since said peptide is considered to play a key role in the development of neurodegenerative processes in said disease.

The articles by J. A. Hardy et al., Science, 2002, 297: 353-356, and D. J. Selkoe, J. Clin. Invest., 2002, 110: 1375-1381, describe that β-amyloid peptide deposits are one of the main causes of neuronal death in AD.

The development of drugs designed for the treatment of AD based on the β-amyloid peptide hypothesis has been the subject of numerous patent applications, which include:

Patent application PCT WO-A-2007/017511 discloses new substituted 1,2-ethylenediamine derivatives for the treatment of Alzheimer's disease. Said compounds act as inhibitors of the β-secretase cleavage of the β-amyloid peptide precursor. Patent applications PCT WO-A-2007/017510, WO-A-2007/017509 and WO-A-2007/017507 also disclose substituted 1,2-ethylenediamines.

Patent application PCT WO-A-2007/034329-A2 discloses new piperazine derivatives for the treatment of Alzheimer's disease which also present inhibitory activity against β-secretase.

Patent application PCT WO-A-2006/085149 discloses adamantane derivatives with an amino group and piperazines for the treatment of illnesses related to the β-amyloid peptide, such as, for example, Alzheimer's disease.

Patent application PCT WO-A-2005/079779 discloses 1-aminocyclohexane derivatives for the treatment of Alzheimer's disease. Said compounds are NMDA receptor antagonists and act as inhibitors of the formation of the β-amyloid peptide and also modify the fibrillogenic deposition thereof.

European patent application EP-A-1305306 discloses 2-adamantyl ethylamine derivatives for the treatment of Alzheimer's disease which act as NMDA receptor antagonists.

European patent application EP-A-1143964 discloses 2-adamantane methylamine derivatives which present NMDA receptor antagonist activity and are used for the treatment of anomalies in glutamatergic transmission, including Alzheimer's disease.

European patent application EP-A-0392059 discloses the use of aminoadamantanes which act as NMDA receptor antagonists and have an anticonvulsant effect, for which reason they are appropriate for the prevention and treatment of cerebral ischaemia.

Patent application WO-A-2007/034329 discloses new compounds derived from substituted quinolines for the treatment of disorders caused by the β-amyloid peptide.

Currently, there are no effective treatments to stop, prevent or reverse the progression of AD.

On the other hand, epilepsy comprises a broad set of disorders which may affect millions of people worldwide. The current therapy is symptomatic and many people suffer from attacks that cannot be controlled with the current anti-epileptic drugs.

There is no prophylactic treatment available for epilepsy, or for the healing of said disorders, except for the neurosurgical resection of epileptic tissue in selected cases.

The article by A. Behrens et al., EMBO Journal, 2007, 26, 4891-4901, discloses that the activation of the protein kinase Erk 1/2 seems to be sufficient to trigger epilepsy in mice and, therefore, it is conceivable that this mechanism may play a significant role in the etiology of some forms of epilepsy in humans.

Consequently, there is a need to develop potent inhibitors of the activation of the Erk 1/2 signalling pathway which are useful for the treatment of diseases associated with the tPA-induced activation of the protein kinase Erk 1/2.

OBJECT OF THE INVENTION

The object of the invention is the compound of formula (I) or a pharmaceutically acceptable salt thereof to be used as a medicine.

Another aspect of the object of the invention is the compound of formula (I) or a pharmaceutically acceptable salt thereof to be used in the treatment of a disease mediated by the protein kinase Erk 1/2 in a patient.

Also a part of the object of the invention is the use of a therapeutically effective quantity of the compound of formula (I) or a pharmaceutically acceptable salt thereof for the preparation of a drug designed for the treatment of a disease mediated by the activation of the protein kinase Erk 1/2 in a patient.

Also a part of the object of the invention is a pharmaceutical composition that contains a therapeutically effective quantity of the compound of formula (I) or a pharmaceutically acceptable salt thereof, and a pharmaceutically acceptable excipient.

DETAILED DESCRIPTION OF THE INVENTION

The authors of this invention have identified that the compound of formula (I) efficiently inhibits the activation of the protein kinase Erk 1/2.

Thus, the object of the invention is the compound of formula (I)

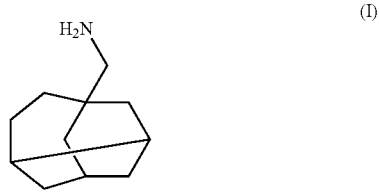 [SMILES: NCC12CCC3CC(CC3C1)C2]

(I)

or a pharmaceutically acceptable salt thereof to be used as a medicine.

Compound of formula (I)

The compound of formula (I) is a product that is commercially available through The company Chemdiv under the denomination 0417-1806.

Within the context of the invention, the compound of formula (I) includes the pharmaceutically acceptable salts, solvates and any stereoisomer or mixture of stereoisomers thereof.

Pharmaceutically acceptable salts of the compound of the invention include those originating from pharmaceutically acceptable organic and inorganic acids. Examples of appropriate acid salts include acetate, adipate, alginate, aspartate, benzoate, benzenesulfonate, bisulfate, butyrate, citrate, camphorsulfonate, cyclopentylpropionate, digluconate, dodecyl sulfate, ethanesulfonate, 3-phenylpropionate, formate, phosphate, fumarate, glucoheptanoate, glycerol phosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalene sulfonate, nicotinate, nitrate, pectinate, persulfate, picrate, pivalate, propionate, salicylate, succinate, sulfate, tartrate, thiocyanate, tosylate and undecanoate.

Use of the Compound of Formula (I)

As already mentioned, the object of the invention includes the use of the compound of formula (I) as a medicine.

Another aspect of the object of the invention also includes the compound of formula (I) or a pharmaceutically acceptable salt thereof to be used in the treatment of a disease mediated by the activation of the protein kinase Erk 1/2 in a patient.

Within the context of the invention, the term "patient" means an animal, preferably a mammal and, more preferably, a human being, and the term "treatment" refers to a prophylactic and/or therapeutic treatment.

Preferably, the disease mediated by the activation of the protein kinase Erk 1/2 is a neurodegenerative illness; more preferably, it is an illness selected from the group formed by Alzheimer's disease and related dementias, epilepsy, Parkinson's disease, Huntington's disease or stroke; even more preferably, it is selected from Alzheimer's disease and related dementias, and epilepsy; and, even more preferably, it is Alzheimer's disease and related dementias, or epilepsy.

Within the context of the invention, related dementias are understood to mean those dementias that are characterised by a loss of memory and the capacity for reasoning, and the neuropathology whereof is associated with the formation of β-amyloid peptide plaques and fibrillary tangles in the brain, with a concomitant reduction in the cholinergic markers in the brain. Persons skilled in the art know of the existence of laboratory tests designed to determine the content of certain indicators in bodily fluids which facilitate the diagnosis of said dementias, as described in R. Guevara et al., Gac. Med. Mex., 2000, 136 (6), 573-584.

Another aspect of the invention also relates to the use of a therapeutically effective quantity of the compound of formula (I) or a pharmaceutically acceptable salt thereof for the preparation of a drug designed for the treatment of a disease mediated by the activation of the protein kinase Erk 1/2 in a patient.

Preferably, the disease mediated by the activation of the protein kinase Erk 1/2 is a neurodegenerative illness; more preferably, it is an illness selected from the group formed by Alzheimer's disease and related dementias, epilepsy, Parkinson's disease, Huntington's disease or stroke; even more preferably, it is selected from Alzheimer's disease and related dementias, and epilepsy; and, even more preferably, it is Alzheimer's disease and related dementias, or epilepsy.

Depending on the particular disease mediated by the activation of the protein kinase Erk 1/2, the drug comprises an additional therapeutic agent, which is normally administered to treat or prevent said disease, jointly with the compound of formula (I) of the invention.

In this regard, for example, the article by I. Churcher, Curr. Top. Med. Chem., 2006, 6, 579-595, concludes that it is unlikely that the treatment of Alzheimer's disease may be based on monotherapy; therefore, the treatment with acetylcholinesterase inhibitors will be combined with other agents, which include anti-amyloid therapies and perhaps anti-tau therapies.

Other examples of therapeutic agents wherewith the inhibitor of this invention may be combined include, without being limited thereto, anti-inflammatory agents such as corticosteroids, TNF blockers, IL-1 RA, azathioprine, cyclophosphamide and sulfasalazine; immunomodulating and immunosuppressant agents, such as cyclosporine, tacrolimus, rapamycin, mycophenolate mofethyl, interferons, corticosteroids, cyclophosphamide, azathioprine and sulfasalazine; neurotrophic factors such as acetylcholinesterase inhibitors, MAO inhibitors, interferons, anticonvulsants, ion channel blockers, riluzole and anti-Parkinson agents; agents designed for the treatment of cardiovascular diseases, such as betablockers, ACE inhibitors, diuretics, nitrates, calcium channel blockers and statins; agents designed for the treatment of hepatic diseases, such as corticosteroids, cholestyramine, interferons and antiviral agents; agents designed for the treatment of blood disorders, such as corticosteroids, anti-leukemic agents and growth factors; agents designed for the treatment of diabetes, such as insulin, insulin analogues, alpha-glucosidase inhibitors, biguanides and insulin sensitisers; and agents designed for the treatment of immunodeficiency disorders, such as gamma globulin.

These additional therapeutic agents may be administered separately from the composition that contains the inhibitor of the activation of the protein kinase Erk 1/2, as a part of a multiple-dosage regimen. Alternatively, these agents may be a part of a single-dosage form, mixed with the inhibitor in a single composition.

The invention also relates to a method for the treatment of a disease mediated by the activation of the protein kinase Erk 1/2 in a patient.

Preferably, the disease mediated by the activation of the protein kinase Erk 1/2 is a neurodegenerative illness; more preferably, it is an illness selected from the group formed by Alzheimer's disease and related dementias, epilepsy, Parkinson's disease, Huntington's disease or stroke; even more preferably, it is selected from Alzheimer's disease and related dementias, and epilepsy; and, even more preferably, it is Alzheimer's disease and related dementias, or epilepsy.

Said method comprises administering to the patient a therapeutically effective quantity of the compound of formula (I) of the invention, or a pharmaceutically acceptable salt thereof, or a solvate thereof, including any stereoisomer or mixture of stereoisomers, jointly with pharmaceutical excipients or vehicles.

Pharmaceutical Compositions and Dosage

Also a part of the object of the invention is a pharmaceutical composition that comprises a therapeutically effective quantity of the compound of formula (I) or a pharmaceutically acceptable salt thereof, and at least one pharmaceutical excipient.

The therapeutically effective quantity may range between 0.1 mg and 1 g; preferably, between 10 mg and 500 mg; more preferably, between 20 mg and 200 mg, and, even more preferably, between 50 mg and 100 mg.

It must be understood that the specific dosage and treatment regimen for any particular patient will be dependent on a large variety of factors, for example, the age, the body weight, the general health condition, the sex, the diet, the administration period, the excretion velocity, the potential combination of drugs, as well as the judgement of the physician in charge and the severity of the particular illness treated.

With this type of drugs, the daily dose may habitually be reached by means of an upward progression in the quantity of the drug administered.

For example, if the daily dose of the compound of formula (I) is estimated to be 20 mg per day, the treatment may be initiated with 5 mg per day, which is half of a tablet containing 10 mg, during the first week. During the second week, 10 mg per day may be administered in two doses and, during the third week, 15 mg per day may be taken, one 10 mg tablet in the morning and half of a 10 mg tablet in the evening. From the fourth week, the treatment may be continued with the 20 mg per day maintenance dose, one 10 mg tablet twice a day.

The pharmaceutical composition of the invention may further comprise an additional therapeutic agent jointly with the compound of formula (I).

The pharmaceutical composition of the invention may be administered by oral route, by parenteral route, by means of a spray for inhalation, by rectal route, by nasal route or by means of an implanted reservoir.

Within the context of the invention, the term parenteral includes subcutaneous, intravenous, intramuscular, intra-articular, intrasynovial, infrasternal, intrathecal, intrahepatic, intralesional and intracranial injection or infusion techniques. Preferably, the composition of the invention is administered by oral, intraperitoneal or intravenous route.

The composition of the invention may be administered by oral route in any orally acceptable dosage form, such as, for example, in the form of granules, matrix pellets, pellets with an inert core, tablets, pills, hard capsules, soft capsules, chewable capsules, osmotic-release systems, vector systems, syrups or solutions.

The pharmaceutical composition may release the active principle in an immediate, delayed or prolonged manner or in the form of pulses.

The dissolution of the active principle may be favoured by using excipients that allow for the preparation of effervescent compositions. Said pharmaceutical forms, as well as the processes for the preparation thereof, are well-known to persons skilled in the art, and information may be found in the handbook Remington: The Science and Practice of Pharmacy, 20th edition, Lippincott, Williams & Wilkins, Philadelphia, 2000 [ISBN: 0-683-306472].

The excipients used in the composition of the invention are selected according to the form of administration that is intended to be prepared.

In the event that the composition of the invention is in the form of granules, it may contain diluent agents, such as, for example, lactose, corn starch, microcrystalline cellulose, methylcellulose, mannitol, sorbitol, calcium phosphate, inositol, urea, isomaltose, kaolin, levulose, magnesium carbonate, sodium alginate, sodium chloride, xylitol or mixtures thereof; disaggregating agents, for example corn starch, croscarmellose sodium, sodium starch glycolate, sodium alginate, or mixtures thereof; binding agents, for example hydroxypropylcellulose; lubricant and anti-caking agents, for example talc, magnesium stearate, calcium stearate, aluminium stearate, polyoxyethylene glycol, colloidal anhydrous silica, silica gel, stearic acid, Precirol®, sodium benzoate, sodium lauryl sulfate, or mixtures thereof; as well as colouring agents. The granules obtained may be incorporated into hard gelatin capsules.

In the event that the composition of the invention is in the form of controlled-release pellets, the following, for example, may be used: sugar spheres, sucroesters, starch and/or cellulose as the pellet cores, ethylcellulose as an agent designed to control the release of the active principle, a plasticiser agent such as stearic acid, and lubricant and anti-caking agents, such as, for example, talc, magnesium stearate, calcium stearate, stearic acid, Precirol®, sodium benzoate, sodium lauryl sulfate or mixtures thereof. The pellets may be incorporated into hard gelatin capsules.

The pharmaceutical composition of the invention may also be in the form of a chewable capsule. In this case, the capsule content may include a vehicle, for example solid semi-synthetic glycerides, refined soybean oil, corn oil, sesame oil or mixtures thereof; stabilising agents, such as, for example, soy lecithin; sweetening agents, such as, for example, mannitol, aspartame (E-951), acesulfame potassium, potassium cyclamate, sodium saccharin or mixtures thereof; aromas and flavouring agents, such as, for example, vanilla, mint oil, menthol or mixtures thereof. The capsule coating may include gelatin and glycerine as capsule structuring agents; thickening agents, such as, for example, acetylated potato starch (E-1420), oxidised acetylated potato starch (E-1451) or mixtures thereof; plasticiser agents, such as, for example, glycerine, sorbitol, propylene glycol, polyethylene glycol or mixtures thereof; and colouring agents.

The pharmaceutical composition of the invention may also be a soft gelatin capsule. In this case, the capsule may contain a vehicle, for example selected from propylene glycol, polyethylene glycol, purified water, corn oil, sesame oil or mixtures thereof; a stabiliser, such as, for example, glycerine; an agent designed to confer viscosity, such as, for example, copovidone or crospovidone or mixtures thereof; and a pH regulating agent, such as, for example, citric acid, tartaric acid, phosphoric acid, sodium acetate, sodium citrate, sodium hydroxide, disodium hydrogen phosphate or mixtures thereof. On the other hand, the capsule structure may be formed by gelatin and a plasticiser agent, such as, for example, glycerine, sorbitol, propylene glycol, polyethylene glycol or mixtures thereof; and it may contain colouring agents.

The pharmaceutical composition of the invention may be in the form of tablets, dilutable and/or dispersible tablets. In this case, it may contain diluent agents, such as, for example, corn starch, microcrystalline cellulose, mannitol, isomaltose, lactose, magnesium carbonate, dicalcium phosphate, dextrose, sucrose or mixtures thereof; disaggregating agents, such as, for example, corn and potato starch, sodium carboxymethylaminopectin, alginic acid and salts and derivatives thereof, formaldehyde-gelatin, formaldehyde-casein, gelatin, croscarmellose sodium, sodium starch glycolate, microcrystalline cellulose and mixtures thereof; lubricant and anti-caking agents, such as, for example, colloidal anhydrous silica, talc, magnesium stearate, calcium stearate, stearic acid, Precirol®, sodium benzoate, sodium lauryl sulfate or mixtures thereof; and aromatising and colouring agents.

In the event that the tablets are obtained by means of wet granulation, in addition to the aforementioned excipients, the following may be included: binding agents, such as, for example, corn starch, gelatin, hydrolysed gelatin, alginic acid derivatives and cellulose-polyvinylpyrrolidone derivatives; and diluent or dispersant agents, such as, for example, purified water, ethanol, isopropanol, methanol and acetone. Regardless of whether the formation of the tablets is by direct compression, or by dry granulation or wet granulation, the tablets may or may not be coated.

In the event that the tablets include a coating, the process may be performed by means of tableting or the incorporation of film coatings.

The tableting process may use sugar as a coating agent; insulating and impermeabilising agents such as, for example, cellulose acetophthalate, polyvinyl phthalate, acrylic resins; plasticiser agents, such as, for example, phthalic acid alkyl esters, citric acid esters or castor oil; and colouring agents.

In order to incorporate a coating, the following may be used: film-forming polymers, such as, for example, hydroxypropylmethylcellulose, Eudragit® polymers, cellulose acetophthalate, hydroxypropylmethylcellulose phthalates, polyvinyl acetophthalate, alginic acid and the derivatives thereof, cellulose hydrogen phthalate, ethylcellulose; plasticiser agents, such as, for example, propylene glycol, glycerine, triacetin, polyethylene glycol, acetylated monoglycerides, phthalate esters, castor oil, sebacic acid esters, silicones or mixtures thereof; and colouring agents.

The composition of the invention may also be in the form of granules and/or effervescent or bucodispersible tablets. In this case, it contains acid substances, such as, for example, citric, tartaric, malic, fumaric, adipic and succinic acid, acid anhydrides, hydrogenated salts such as sodium dihydrogen phosphate, sodium hydrogen citrate or mixtures thereof; and carbonated compounds, such as, for example, sodium or potassium bicarbonate, sodium or potassium carbonate or mixtures thereof. Moreover, it may contain binding agents, such as, for example, polyvinylpyrrolidone; lubricant agents, such as, for example, polyethylene glycol, sodium benzoate, adipic, succinic or fumaric acid, amino acids or mixtures thereof; and aromatising agents.

The composition of the invention may also involve an osmotic release system. These systems are composed of tablets formed by an osmotic core, which contains the aforementioned compound of formula (I) as the active principle, and are coated with a membrane that is semi-permeable to water and presents a small opening. Said membrane only allows for the free diffusion of water into the inside of the core. The water dissolves the active' principle and creates an osmotic pressure that expels the saturated medicated solution towards the exterior through the membrane opening, by means of zero-order kinetics. These systems may be of two types, with a single compartment (OROS and GITS) or with two compartments separated by a flexible wall, one of them containing the active ingredient and the other containing the osmotic agent.

The composition of the invention may also involve a vector system. These systems involve attaching the active principle to a vector, which will be in charge of transporting the active ingredient to the target organ or cell. For example, fragment C of the tetanus toxin (TTC), which does not have pathogenic power, has a great specificity for the nervous system, for motor neurons, and is therefore capable of performing retrograde intraneural and trans-synaptic transport along the central nervous system.

The sterile injectable forms of the composition of the invention may be aqueous or oily suspensions, and may be formulated according to techniques that are well-known to persons skilled in the art, using dispersant or wetting agents and adequate suspension agents. The sterile injectable preparation may also be a sterile injectable solution or suspension in a non-toxic parenterally acceptable diluent or solvent. The acceptable vehicles and solvents that may be used include water, Ringer's saline solution and isotonic sodium chloride solution. Moreover, conventionally, sterile non-volatile oils may be used as the solvents or suspension media. To this end, any soft non-volatile oil may be used, including synthetic mono- or diglycerides. Fatty acids, such as oleic acid and the glycerol derivatives thereof, are useful in the preparation of injectables; also useful are pharmaceutically acceptable natural oils, such as olive oil or castor oil, especially in their polyoxyethylated versions. These oily solutions or suspensions may also contain a long-chain alcohol diluent or dispersant, such as carboxymethylcellulose or similar dispersant agents that are habitually used to formulate pharmaceutically acceptable dosage forms, including emulsions and suspensions. For formulation purposes, other habitually used surfactants may also be used, such as those commercialised under the names Tween® and Span®, and other emulsifying or bioavailability-enhancing agents, which are habitually used in the manufacturing of Solids, liquids or other pharmaceutically acceptable dosage forms.

The book by R. C. Rowe et al., Handbook of Pharmaceutical Excipients, 4th edition, Pharmaceutical Press, London, 2003 [ISBN: 0-85369-472-9], contains information about the most habitual excipients used in pharmaceutical compositions, including the commercial names and suppliers thereof.

In Vitro Assays

The capacity to inhibit the activation of the protein kinase Erk 1/2 presented by the Compound of formula (I) has been determined by means of the ELISA (Enzyme-Linked Immunoadsorbent Assay) technique, as described in the Examples section.

Under the same assay conditions, we determined the inhibitory efficacy of the active principle memantine and the drug called dizocilpine, also known as MK-801, developed by the company Merck & Co. Memantine is commercialised under the name Axura® by the Merz company, and has been approved in Europe and the US for the treatment of Alzheimer's disease. Compound MK-801 was also proposed for the treatment of Alzheimer's disease and other neurodegenerative illnesses such as Huntington's disease and stroke.

Surprisingly, it was observed that the compound of formula (I) of the invention effectively inhibits the activation of the protein kinase Erk 1/2 induced by the tissue plasminogen activator (tPA), and presents inhibition values comparable to those of the two drugs assayed.

In a second in vitro assay, the apoptosis in nerve cells was measured by means of the TUNEL technique described in R. Sgonc et al., Trends Genetics, 1994, 10, 41-42. Apoptosis is the function that controls the death of a biological unit in a programmed manner.

In this assay, we analysed the apoptosis of neurons cultured in vitro following the treatment with the β-amyloid peptide by itself or in the presence of the inhibitor, and it was surprisingly observed that the compound of formula (I) of the invention also efficiently inhibited the apoptosis induced by the β-amyloid peptide.

The inhibition obtained with the compound of formula (I) was comparable to that obtained with the drug memantine.

The use of these two assays as a model to evaluate the use of the compound of formula (I) in the treatment of neurodegenerative illnesses, in particular Alzheimer's disease, is justified because β-amyloid peptide deposits have been described as one of the main causes of neuronal death in Alzheimer's disease (reviewed in J. A. Hardy et al., Science, 2002; 297: 353-6; D. J. Selkoe, J. Clin. Invest., 2002, 110: 1375-81).

On the other hand, the data published by Medina et al. in the aforementioned article show that the tPA-mediated activation of the protein &rase Erk 1/2 leads to neuronal apoptosis through the β-amyloid peptide. For this reason, inhibition of the activation of the protein kinase Erk 1/2 translates into a blockage of the toxicity of the β-amyloid peptide and, as a consequence, a reduction in the apoptosis of nerve cells.

Since the compound of formula (I) blocks the tPA-induced activation of Erk 1/2 and the toxicity of the β-amyloid peptide, it is reasonably justified that said compound may be of therapeutic use in the treatment of neurodegenerative illnesses, such as, for example, Alzheimer's disease.

The examples below serve to illustrate the invention, but do not limit it in any way.

EXAMPLES

Example 1

ELISA Assay for the Detection of the Activation of Erk 1/2

In the ELISA assays, neurons from primary cultures of hippocampi isolated from mouse embryos (day 16.5 of gestation) were used, following the protocol described by Goslin and Banker (Goslin K and Banker G (1991) Culturing Nerve Cells, MIT Press, Cambridge, Mass.). This culture was used because the hippocampus is the main region affected in Alzheimer's disease and they are non-transformed cells.

10,000 cells/well were seeded in 96 well plates (Nunc) pre-treated with poly-L-Lys (SIGMA) and left under culture for 7 days.

The treatment with tPA was performed by adding it at 20 μg/ml (without changing the medium), for 1 hour. The treatment with the inhibitor, the compound of formula (I), was performed by means of a 15 minutes pre-incubation prior to the addition of tPA, as described above.

Following the treatments, the cells were fixed with methanol at a temperature of −20° C. for 5 min, and an ELISA assay was performed in order to detect the activation of Erk 1/2.

The wells were washed three times with TBST (Tris-buffered saline, 0.1% Triton® X-100) and blocked with 5% horse serum in TBST for 1 h at 37° C. They were once again washed with TBST, 0.35 pg/ml of the corresponding primary antibody (anti-phospho-Erk 1/2 Cell Signalling, catalogue number 9101, 1/500 or total Erk 1/2, Upstate catalogue number 06-182 1/1000 in 3% bovine serum albumin in TBST) were added and it was incubated overnight at 4° C.

After 4 washings with TBST, 0.45 μg/ml of the secondary alkaline-phospatase-coupled anti-rabbit antibody (DAKO, 1/800 in 3% bovine serum albumin in TBST) were added and it was kept for 1 h at 37° C.

4 washings with TBST were performed and it was developed using 4-methylumbelliferyl phosphate as the substrate (1 mg/ml in 0.2 M triethanolamine at pH 8.5) for 30 min at room temperature in the dark.

The results were quantified by means of fluorescence reading using the Cytofluor 235 fluorometer with an excitation filter of 360/40 and an emission filter of 460/40.

All the treatments were performed in sextuplicate in each experiment: 3 points for phosphorylated Erk 1/2 and 3 points for total Erk 1/2. At least 4 independent experiments were performed.

The following were used as controls:
1) cells without treatment (negative control),
2) cells treated with tPA and without an inhibitor (positive control), and
3) cells incubated only with the secondary antibody and the substrate (negative control in the ELISA technique).

Table 1 shows the normalised Erk 1/2 values obtained. The reference was the value of the positive control, cells treated only with tPA, which was given a relative value of 1 (arbitrary unit). The rest of the values are adjusted in relation to this value 1 of tPA.

TABLE 1

| Compound | Mean value (arbitrary units) | Standard deviation |
| --- | --- | --- |
| Negative control | 0.61 | 0.03 |
| tPA (positive control) | 1 | 0.00 |
| Dizocilpine (MK-801) | 0.73 | 0.05 |
| Memantine | 0.75 | 0.05 |
| Compound of formula (I) | 0.61 | 0.09 |

It may be observed that the compound of formula (I) of the invention presents an inhibitory effect on the activation of the protein kinase Erk 1/2 which is comparable to that obtained with the drugs memantine and MK-801, the first of which is already being used in the treatment of neurodegenerative illnesses such as Alzheimer's disease.

Therefore, the compound of formula (I) of the invention presents appropriate characteristics to be considered as a good candidate to be used as an active principle in the treatment of neurodegenerative illnesses, such as, for example, Alzheimer's disease.

Example 2

TUNEL Assay for the Detection of Cellular Apoptosis

Hippocampal neurons (obtained as described in Example 1) were cultured in 24 well plates (Nunc) at a density of 100,000 cells/well.

After 7 days under culture, β-amyloid peptide 1-40 (Aβ1-40) (Amyloid βProtein (1-40) trifluoroacetate salt, Bachem) (20 µM) was added and the cells were incubated for 72 h.

In order to study the inhibitory effect of the compound of formula (I), the cells were pre-incubated for 15 minutes with said compound at a concentration of 30 µM prior to the addition of the β-amyloid peptide, Aβ1-40.

After 72 h, the cells were fixed and the apoptotic neurons were detected by means of the TUNEL technique (Sgonc, R. et al. (1994) Trends Genetics 10, 41-42) with the in situ "cell death detection" kit, POD (Roche). In said kit, fluorescein-dUTP was used to label the DNA chain cleavage, which makes it possible to directly visualise the staining of the nuclei of the apoptotic neurons in the fluorescence microscope.

Parallel to this, the neuronal nuclei were stained with a specific monoclonal antibody (mouse anti-neuronal nuclei (NeuN) monoclonal antibody, 0.5 µg/ml, Chemicon) and a secondary anti-mouse Cy3 antibody (3.75 µg/ml, Jackson Immunoresearch Laboratories).

The quantification was performed by counting the positive nuclei following the TUNEL staining in 3 random fields and expressed as the % of dead neurons with respect to the total number of neurons in each field. Each inhibitor was assayed in triplicate in 4 independent experiments.

As a negative control, cells cultured for the same period of time, without treatment with the β-amyloid peptide (measurement of baseline spontaneous apoptosis), were used. As a positive control of 100% apoptosis, treatment with DNAse (20 U/ml) was used, following the procedure indicated in the commercial kit.

Table II shows the results of the apoptosis of nerve cells. The value of the positive control (treatment with DNAse) was considered to be 100 and the rest of the measurements were adjusted in relation to this value.

TABLE II

| Compound | Mean value (%) | Standard deviation |
|---|---|---|
| Negative control | 0.4 | 0.2 |
| Positive control | 100 | 0.00 |
| β-amyloid peptide (Aβ1-40) | 83.8 | 1.6 |
| Memantine | 4 | 0.4 |
| Compound of formula (I) | 2.8 | 0.3 |

It may be observed that the percentage of dead cells as a result of the β-amyloid peptide is considerably reduced when the compound of formula (I) is used as an inhibitor.

Therefore, the compound of formula (I) of the invention is a good candidate to be used as an active principle for the treatment of neurodegenerative illnesses, such as, for example, Alzheimer's disease.

The invention claimed is:

1. A compound having the formula

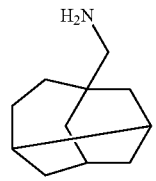

or a pharmaceutically acceptable salt thereof.

2. A method for the treatment of a disease mediated by the activation of the protein kinase Erk 1/2 in a patient comprising administering the compound of claim 1.

3. The method of claim 2 wherein the disease mediated by the activation of the protein kinase Erk 1/2 is a neurodegenerative illness.

4. The method of claim 3, wherein the disease is selected from the group formed by Alzheimer's disease and related dementias, epilepsy, Parkinson's disease, Huntington's disease or stroke.

5. The method of claim 4, wherein the disease is selected from the group formed by Alzheimer's disease and related dementias, and epilepsy.

6. The method of to claim 5, wherein the disease is Alzheimer's disease and related dementias.

7. The method of claim 5, wherein the disease is epilepsy.

8. The method of claim 2 wherein said compound comprises an additional therapeutic agent.

9. A pharmaceutical composition characterised in that it comprises a therapeutically effective quantity of the compound of claim 1 or a pharmaceutically acceptable salt thereof, and at least one pharmaceutical excipient.

10. The pharmaceutical composition according to claim 9, further comprising an additional therapeutic agent.

11. The method of claim 2 wherein the compound is administered by oral route, by parenteral route, by means of a spray for inhalation, by rectal route, by nasal route, or by means of an implanted reservoir.

* * * * *